(12) United States Patent
Charles

(10) Patent No.: US 7,153,138 B2
(45) Date of Patent: Dec. 26, 2006

(54) HEALTH MANAGEMENT CUFF

(76) Inventor: Chelsea Charles, 385 Bluff Ridge Cove, Cardova, TN (US) 38018

(*) Notice: Subject to any disclaimer, the term of this patent is extended or adjusted under 35 U.S.C. 154(b) by 236 days.

(21) Appl. No.: 10/951,152

(22) Filed: Sep. 27, 2004

(65) Prior Publication Data

US 2005/0069844 A1     Mar. 31, 2005

Related U.S. Application Data

(60) Provisional application No. 60/506,542, filed on Sep. 26, 2003.

(51) Int. Cl.
*G09B 19/00* (2006.01)
(52) U.S. Cl. ............... 434/127; 434/236
(58) Field of Classification Search ............ 434/127, 434/203, 204, 236, 246; 235/61 R, 123, 235/1 B
See application file for complete search history.

(56) References Cited

U.S. PATENT DOCUMENTS

| | | | | |
|---|---|---|---|---|
| 1,525,005 A | * | 2/1925 | Sherman | ............... 63/3.1 |
| 1,567,021 A | * | 12/1925 | Detlefsen et al. | ............ 63/1.11 |
| 4,210,093 A | * | 7/1980 | Baker | ............... 116/222 |
| 4,335,300 A | * | 6/1982 | Shepherd | ............... 235/123 |
| 4,448,579 A | * | 5/1984 | Currie | ............... 434/203 |
| 4,599,508 A | | 7/1986 | Smetaniuk | |
| 4,812,124 A | * | 3/1989 | Colodner et al. | ............ 434/203 |
| 4,912,307 A | | 3/1990 | Shade et al. | |
| 4,912,944 A | | 4/1990 | Crosley et al. | |
| 4,965,553 A | | 10/1990 | DelBiondo, II et al. | |
| 4,993,952 A | | 2/1991 | Yeh | |
| 5,190,459 A | * | 3/1993 | Determan | ............... 434/238 |
| 5,205,747 A | * | 4/1993 | Tan | ............... 434/203 |
| 5,338,202 A | | 8/1994 | Saari | |
| 5,382,165 A | | 1/1995 | Knox | |
| 5,412,560 A | | 5/1995 | Dennison | |
| 5,451,079 A | | 9/1995 | Gong et al. | |
| 5,796,640 A | | 8/1998 | Sugarman et al. | |
| 5,890,128 A | | 3/1999 | Diaz et al. | |
| 5,915,854 A | | 6/1999 | Burke et al. | |
| 6,223,559 B1 | | 5/2001 | Coleman | |
| 6,279,958 B1 | | 8/2001 | Santa Cruz et al. | |
| 6,341,295 B1 | | 1/2002 | Stotler | |
| 6,431,873 B1 | | 8/2002 | Flagg | |
| 6,478,736 B1 | | 11/2002 | Mault | |
| 6,551,110 B1 | * | 4/2003 | Hastie | ............... 434/365 |
| 6,561,415 B1 | | 5/2003 | Grant | |
| 6,569,039 B1 | | 5/2003 | Cope | |

(Continued)

*Primary Examiner*—Kurt Fernstrom
(74) *Attorney, Agent, or Firm*—Howard & Howard Attorneys, P.C.

(57) ABSTRACT

A cuff (10, 110, 210, 310) for a health managing system includes a strand (14, 114, 214, 314) having first (16, 116, 216, 316) and second (18, 118, 218, 318) strand sections interconnected to define a loop (128, 228, 328). A plurality of beads (30, 130, 230, 330), each presenting a numerical or a non-numerical value, are slidably retainable and movable along the strand (14, 114, 214, 314). A pair of curved resilient members (38, 138, 238, 338) are interconnected with the first (16, 116, 216, 316) and second (18, 118, 218, 318) strand sections by fasteners (50, 150) to form a strand segment or compressible mechanical device (36, 136, 336) for providing a difference in resistance to movement of the beads (30, 130, 230, 330) along the first (16, 116, 216, 316) and second (18, 118, 218, 318) strand sections than along the device (36, 136, 336). Alternatively, the strand segment may include a magnetic section (263) disposed between the first (216) and second (218) strand sections.

28 Claims, 3 Drawing Sheets

U.S. PATENT DOCUMENTS 6,626,757 B1    9/2003  Oliveras
6,699,044 B1 *  3/2004  Lang .......................... 434/246
6,747,917 B1 *  6/2004  Jennings et al. ............. 368/10

2002/0055087 A1    5/2002  Hardesty
2003/0111005 A1 *  6/2003  Lord et al. .................. 116/307

* cited by examiner

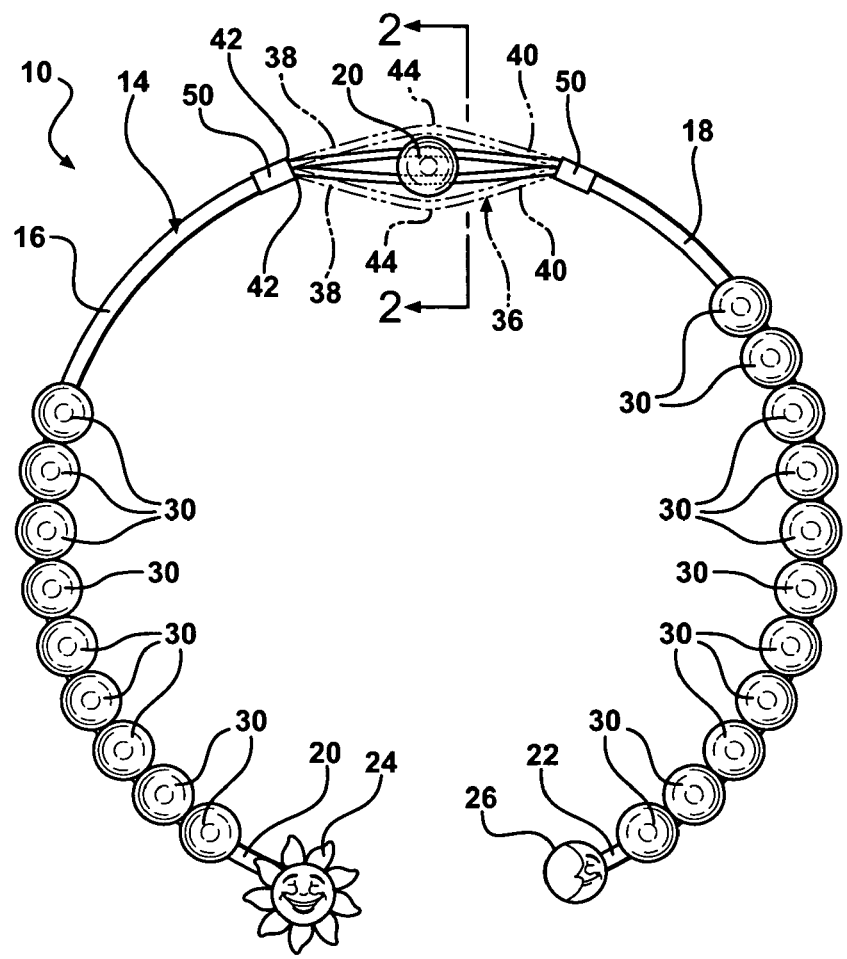
FIG - 1
FIG - 2
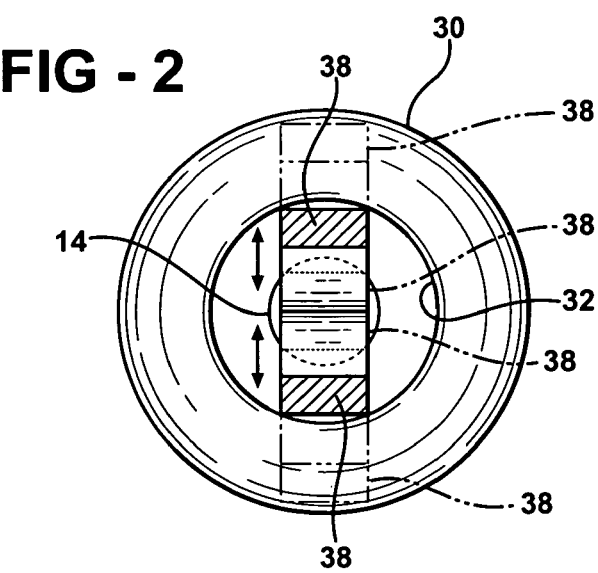

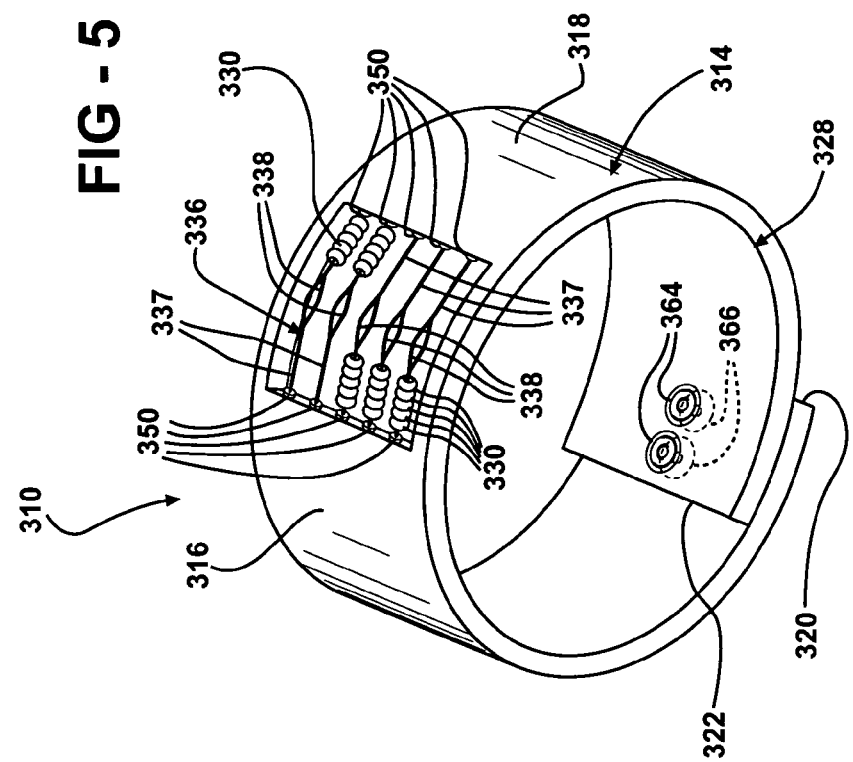
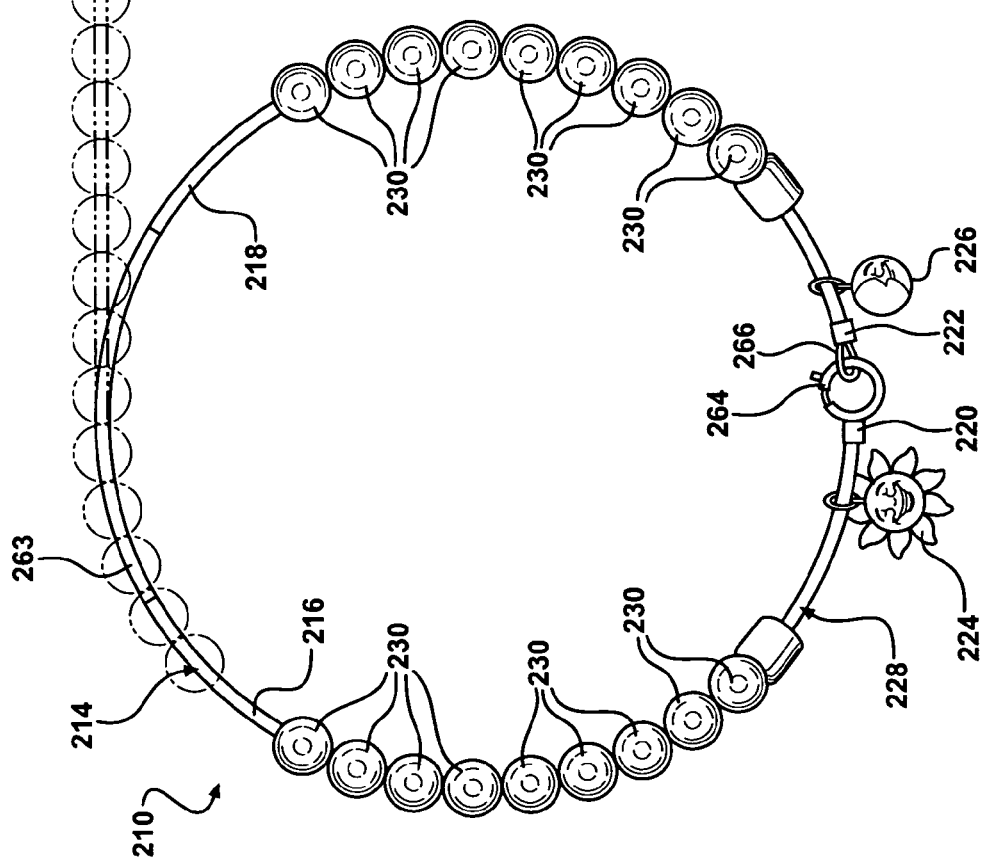

HEALTH MANAGEMENT CUFF

RELATED APPLICATIONS

This application claims priority to U.S. Provisional Patent Application Ser. No. 60/506,542 filed Sep. 26, 2003.

FIELD OF THE INVENTION

The subject invention relates generally to an accessory item and, more particularly, to a dieting aid or a dieting system inclusive of a calorie-counting bracelet.

BACKGROUND OF THE INVENTION

Today, people are heavier than ever before. Poor diet and physical inactivity, two major contributors to obesity, are closing in on tobacco use as the leading preventable causes of death in the United States, according to a report in March in the Journal of the American Medical Association. Also, since people place so much emphasize on appearance, often added pounds create a negative self-image resulting in depression and an overall lack of motivation to better their lives. When the money spent attempting to fix the health-related damages of obesity is added with that spent on our society's constant desire to be svelte, it equals a multi-billion dollar weight-loss industry. People will go to extremes to lose weight; attempting things like, juice fasts, life-threatening diet pills, fad diets, and exercise binges.

But, despite the miracle-promising weight loss scheme introduced each day, people continue to gain weight at an alarming rate. Usually two things happen when they embark on the fad diet. First thing relates to loss of interest because the diet method or tool cannot fit into their everyday lives. Second, even if weight is lost, it eventually returns with a vengeance due to boredom or exhaustion with the weight-loss tool and/or program. So despite the miracle promises, the only proven, sure ways to lose weight and keep it off are a combination of exercises and combined monitoring of both calorie and carbohydrate consumption. Fitness experts recommend keeping a food diary to write down everything, as soon as it is consumed. There are also software programs and electronic adding machines to count the number of calories if one knows the content of the items consumed. Unless there is a visible, constant reminder throughout the day, these tools won't be utilized. In order for a weight loss tool to be successful in this fast-paced, image-driven society it must adapt to people of different lifestyles and fashion tastes, at different stages of their lives; promote health and discipline without resulting in extreme deprivation. In addition.

Various dieting devices and methods have been taught by the U.S. Pat. No. 5,338,202 to Saari; U.S. Pat. No. 5,382,165 to Knox; U.S. Pat. No. 5,915,854 to Burke et al.; U.S. Pat. No. 5,796,640 to Sugarman et al.; and U.S. Pat. No. 6,341,295 to Stotler. One such example, disclosed in the U.S. Pat. No. 5,338,202 to Saari, teaches a planner having a foldable carrying case with a plurality of pockets and pocket inserts, or meal insert cards on and in the inside walls of the carrying case. Each meal insert cards identifies a specific meal type such as, for example, a dinner or a breakfast. A plurality of food cards each listing one specific food within a food exchange and displaying a picture of either the approximate or visual serving size of the food. A user selects the food cards each listing one specific food and places them in the pockets for the type of the meal. One of the prime shortcomings of the aforementioned calorie counting devices is their unattractiveness and blatant purpose. Most people today simply do not want to advertise the fact that they are dieting, let alone wear an unattractive numeric-indicator or planner for displaying the thousands of calories consumed in a day.

Alluding to the above, a bracelet, taught by the U.S. Pat. No. 6,561,415 to Grant, tried to solve the aforementioned problem. The bracelet includes sliding attached beads, intermittent "summing" beads, and a printed plastic wallet card that indicates the bead values for commonly eaten foods. The beads are assigned a value of 100 calories per bead and are subdivided into groups of summing beads. For every 100 calories consumed, one bead is moved across the bracelet. The bracelet taught by the U.S. Pat. No. 6,561,415 to Grant does not prevent the backwards and/or forward movement of beads, which results in uncontrolled movement of the beads through strenuous exercise or daily routine. In addition, the bracelet is unattractive and does not work with every type of outfit for a variety lifestyles. In addition, a tracking space defined between the beads is about half on an inch, which results in an unpleasantly looking bracelet.

But even, if it is practicable, it would be desirable to provide an improved bracelet or a cuff that fully prevents the backwards and/or forward movement of beads, thereby controlling "bead slide" created by through strenuous exercise or daily routine. It would also be beneficial to present an attractive accessory to work with every type of outfit for a variety lifestyles.

SUMMARY OF THE INVENTION

A health management cuff of the present invention includes a strand having first and second terminal ends. A plurality of beads are retained on the strand and are slidably movable between the first and second terminal ends. A dividing segment is disposed along the strand dividing the strand into opposing strand sections and providing a difference in resistance to movement of the plurality of beads along the opposing strand sections from the dividing segment, thereby retaining the plurality of beads on one of the opposing strand sections.

An advantage of the present invention is to provide the cuff having a segment section, which provides a difference in resistance to movement of the beads along the strand sections than along the dividing segment, thereby preventing the backwards and/or forward movement of beads through strenuous exercise or daily routine.

Another advantage of the present invention is to provide the cuff which is attractive and fits with every type of outfit for individuals' varying lifestyles.

Still another advantage of the present invention is to provide the cuff which is a cost-effective, safe, and simple tool created to aid weight-loss and style for males and females of all ages.

BRIEF DESCRIPTION OF THE DRAWINGS

FIG. 1 shows a health management cuff comprising a plurality of beads and a device disposed on the cuff for controlling movement of the beads along the cuff;

FIG. 2 shows a sectional view of the bead of FIG. 1, with the device extending through the bead with the device movable from a blocking position, shown in phantom, to a sliding position;

FIG. 4 shows a second alternative embodiment of the cuff shown in FIG. 1, and

FIG. 5 shows a third alternative embodiment of the cuff shown in FIG. 1.

DESCRIPTION OF THE INVENTION

Figure 3:
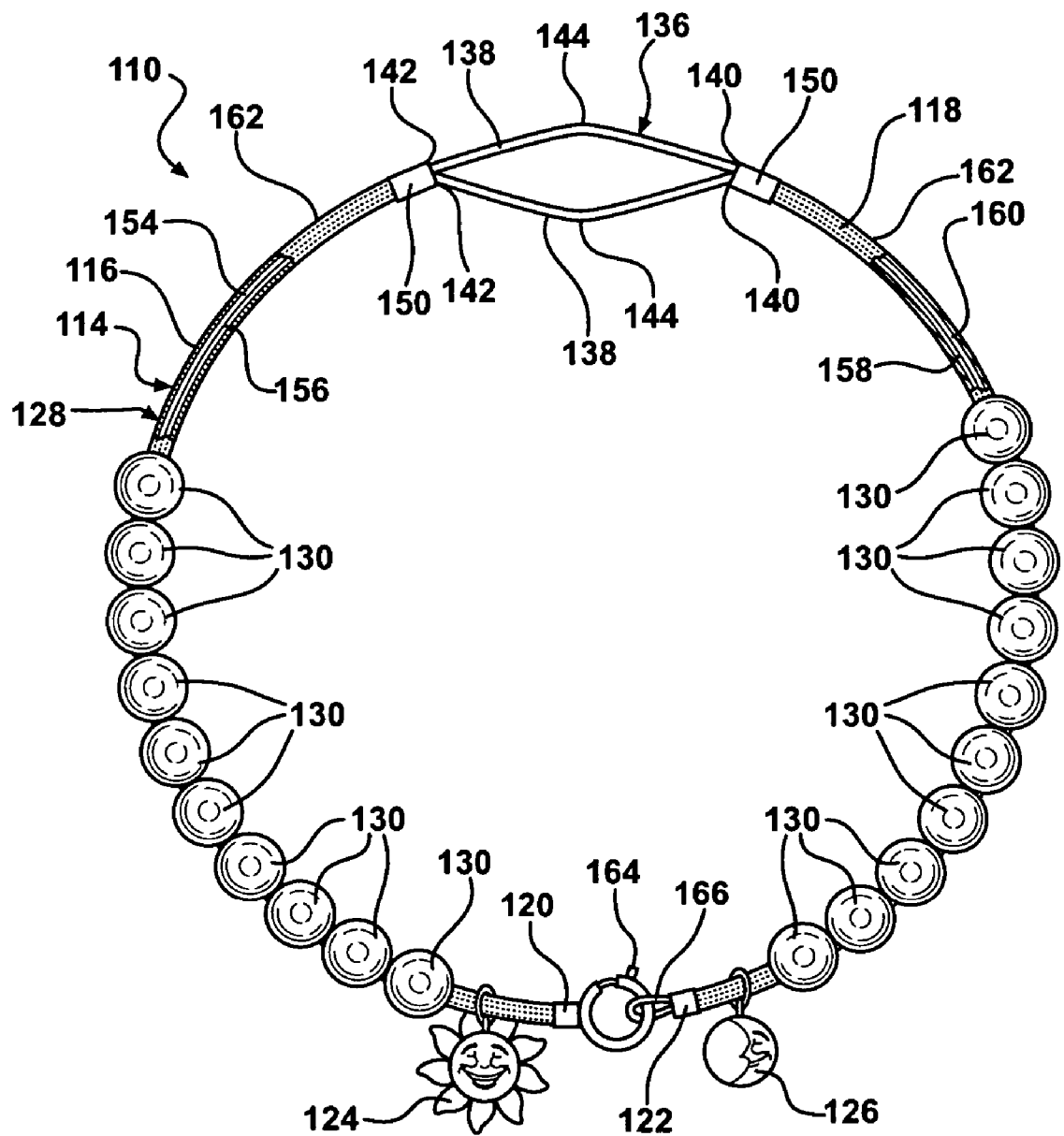
FIG. 3 shows a first alternative embodiment of the cuff shown in FIG. 1.

Referring to FIG. 1, an inventive health management cuff for a health management system is generally shown at 10. The cuff 10 includes a strand, generally indicated at 14 having first 16 and second 18 strand sections each presenting terminal ends 20 and 22, respectively. Preferably, the first and second strand sections 16 and 18 present a circular configuration. However, other configurations of the strand 14 are contemplated by the present invention. Preferably, each first and second strand sections 16 and 18 may include a charm bead 24 of one kind, as identifying a first part (A.M.) of a day and a charm bead of another kind 26, identifying a second part (P.M.) of the day. Both charm beads 24 and 26 are mechanically disposed at the respective terminal ends 20 and 22 to assist a user (not shown) in tabulating the health managing system when counting intake of the calories, or, for example, when taking a medicine.

A plurality of beads 30 or charms are retained along the strand 14 and are movable between the first and second strand sections 16 and 18. Preferably, the number of beads 30 is twenty to form the aforementioned health managing system, wherein each bead 30 signifies a fragmental numerical or non-numerical value of the health managing system. Alternatively, the number of beads 30 may be adjusted as the user may desire. For example, each bead 30 signifies 100 calories or a number of carbohydrates, depending on what phase the user is at his/her diet. As shown in FIG. 2, each bead 30 includes an opening 32 adaptable to receive the strand 14 extending therethrough. Preferably, each bead 30 presents a round configuration. Alternatively, each bead 30 may present a form of a cube, a cylinder, or the like (not shown). Each bead 30 may be formed from a metal, a polymer, a wood, or the like.

Referring back to FIG. 1, a dividing segment defined by a device, generally indicated at 36 is disposed between first and second strand sections 16 and 18. The device 36 comprises a pair of curved resilient members 38 each presenting terminal ends 40 and 42. Each member 38 presents a peak 44 and is compressible between curved and planar positions, as shown in FIG. 1, as an external force is applied to the member 38 in a manner to be described furtherbelow. A pair of fasteners 50 clamp the spaced resilient members 38 at the respective terminal ends 40 and 42 interconnecting the spaced resilient members 38 to the first and second strand sections 16 and 18 of the cuff 10. Each resilient member 38 diverges from one of the fasteners 50 to the respective peak 44 and then extends from the respective peak 44 to another of the fasteners 50 forming a diamond-shaped frame, generally indicated at 52 of the device 36.

As best shown in FIG. 2, when the external force is applied to the spaced resilient members 38, each resilient member 38 compresses relative to one another, shown in phantom, to define a sliding position to allow the beads 30 to sequentially move between the first and second strand sections 16 and 18. When the external force is not applied, each spaced resilient member 38 is de-compressed from the aforementioned sliding position to a blocking position thereby blocking movement of the beads 20 between the first and second strand sections 16 and 18.

Typically, the user counts calories ingested based on assigned quantitative caloric values of each bead 30. Once food is ingested, the user slides the appropriate number of beads 30 along the device 36 from the first strand section 16 to the second strand section 18 of the cuff 10 for later count. At the end of the day, the user sums the total calories ingested through enumeration of beads 30 slid from one of the segment sections 16 of the cuff 10 to another 18 as compared with their assigned quantitative values. Finally, the user moves the counting beads 30 back to their original position to begin counting the next day.

Alluding to the above, a first alternative embodiment of the present invention is generally shown at 110 in FIG. 3, wherein like reference numerals are used to indicate like features with regard to the main embodiment, but are offset by 100. The first alternative embodiment presents the first 116 and second 118 strand sections defined by a pair of wires 154, 156 forming the first strand section 116 and another pair of wires 158, 160 forming the second strand section 118 with each pairs extending transversely with respect to one another with the wires 154, 156, 158, 160 being interconnected with the resilient members 138 by the fasteners 150. Alternatively, each pair of wires 154, 156, 158, 160 may include a pair of silver band or sleeve 162 with the wires 154, 156, 158, 160 extending therethrough. The beads 130 are slidably disposed along the sleeves 162 but are prevented from moving between the first 116 and second 118 strand section as resistance of the device 136 is applied.

The cuff 110 may include a male connector 164 and a female connector 166 each connected to the first and second strand sections 116 and 118 at the respective terminal ends 120 and 122 to mechanically engage the first and second strand sections 116 and 118 to form a loop, generally indicated at 128. Such male 164 and female 166 connectors are further defined by a pair of opposite jump rings, known to those skilled in the art, to provide a convenient means of attachment between the first and second strand sections 116 and 118. Each first and second strand sections 116 and 118 may include the charm bead 124 of one kind, as identifying a first part (A.M.) of a day and a charm bead of another kind 126, identifying a second part (P.M.) of the day connected to the first and second strand section 116 and 118 in the aforementioned manner to assist the user in tabulating the health managing system when counting intake of the calories, or, for example, when taking the medicine.

Referring to FIG. 4, a second alternative embodiment of the present invention is generally shown at 210, wherein like reference numerals are used to indicate like features with regard to the main embodiment, but are offset by 200. The second alternative embodiment includes the first and second strand sections 216 and 218 of the strand 214 formed from a non-magnetic material. The beads 230 are supported on the first and second strand sections 216 and 218 in the aforementioned manner. A magnetic strand segment or section 264 is disposed between the first and second strand sections 216 and 218 interconnecting the first and second strand sections 216 and 218. Alternatively, the beads 230 and the first and second strand sections 216 and 218 may be formed from a magnetic material with the section 264 from a non-magnetic material. Alternatively, the magnetic section 264 may be defined by a sleeve (not shown) formed from a magnetic material to receive the strand 214 with the sleeve mechanically connected to the strand 214. In this embodiment, the movement of the beads 230 is blocked by the magnetic section 263 or the sleeve during various strenuous exercises or daily routine, thereby preventing the backwards or forward movements of the magnetic beads 230.

The cuff 210 may include a male connector 264 and a female connector 266 each connected to each of the first and second strand sections 216 and 218 at the respective terminal ends 220 and 222 to mechanically engage the first and second strand sections 216 and 218 to form a loop, generally indicated at 228. Such male 264 and female 266 connectors are further defined by a pair of opposite jump rings, known to those skilled in the art, to provide a convenient means of attachment between the first and second strand sections 216 and 218. Each first and second strand sections 216 and 218 may include the charm bead 224 of one kind, as identifying a first part (A.M.) of a day and a charm bead of another kind 226, identifying a second part (P.M.) of the day connected thereto in the aforementioned manner to assist the user in tabulating the health managing system when counting intake of the calories, or, for example, when taking the medicine.

Referring to FIG. 5, a third alternative embodiment of the present invention is generally shown at 310, wherein like reference numerals are used to indicate like features with regard to the main embodiment, but are offset by 300. The third alternative embodiment includes the first and second strand sections 316 and 318 of the strand, generally indicated at 314, formed from leather, a synthetic material, or the like. The device, generally indicated at 336, is disposed between the first and second strand sections 316 and 318 of the strand 314 interconnecting the first and second strand sections 316 and 318. The device 336 is further defined by a plurality of spaced tracks or wires 337 extending between the first and second strand sections 316 and 318 and connected to the first and second strand sections 316 and 318 by the fasteners 350.

Preferably, the plurality of the spaced wires is further defined by five wires 337. However, there may be more or less than five wires 337. Each wire 337 signifies a meal period within twenty four hour day. Each wire 337 includes a pair of curved resilient members 338 dividing each wire 337 into opposing halves. Each curved resilient member 338 presents terminal ends 340 and 342 and forms a diamond-shaped frame as the curved resilient member 338 are non-compressed, similar to the aforementioned embodiment of the present invention, as shown in FIGS. 1 and 3. Each wire 337 may include four of five beads 330 with all wires 337 comprising between twenty to twenty five beads 330. However, the number of beads 330 and/or wires 337 is not intended to limit the present invention.

The cuff 310 may include a plurality of male connector 364 and a plurality of female connectors, shown in phantom at 366, each connected to the first and second strand sections 316 and 318 at the respective terminal ends 320 and 322 to mechanically engage the first and second strand sections 316 and 318 to form a loop, generally indicated at 328 of various sizes. Such male 364 and female 366 connectors are known to those skilled in the art and provide a convenient means of attachment between the first and second strand sections 316 and 318. Alternatively, each first and second strand sections 316 and 318 may include the charm bead (not shown) of one kind, as identifying a first part (A.M.) of a day and a charm bead of another kind (not shown), identifying a second part (P.M.) of the day connected thereto in the aforementioned manner to assist the user in tabulating the health managing system when counting intake of the calories, or, for example, when taking the medicine or the meal.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A health management cuff comprising;
a strand having first and second terminal ends,
a plurality of beads retained on said strand for movement along said strand between said first and second terminal ends,
a dividing segment disposed along said strand dividing said strand into opposing strand sections and providing a difference in resistance to movement of said beads along said opposing strand sections from said dividing segment, thereby retaining said plurality of beads on one of said opposing strand sections.

2. A health management cuff as set forth in claim 1 wherein said dividing segment is further defined by a device disposed on said strand and movable between a first position to prevent movement of said beads between said first and second terminal ends and a second position with said beads sequentially movable between said first and second terminal ends for tabulating a health management system.

3. A health management cuff as set forth in claim 2 wherein said device is further defined by a pair of curved resilient members each presenting terminal ends.

4. A health management cuff as set forth in claim 3 wherein said device further includes a pair of fasteners with each fastener clamping said spaced resilient members at the respective terminal ends thereby connecting said spaced resilient members to said strand.

5. A health management cuff as set forth in claim 4 wherein each said resilient member defines a peak thereby forming a generally diamond-shaped frame of said device as said device is compressed in said second position.

6. A health management cuff as set forth in claim 5 wherein said opposing strand sections are formed from a metal.

7. A health management cuff as set forth in claim 6 wherein said metal is non-magnetic.

8. A health management cuff as set forth in claim 7 wherein said opposing strand sections are further defined by a plurality of wires extending between one of said fasteners and one of said terminal ends.

9. A health management cuff as set forth in claim 8 including a pair of sleeves surrounding said wires.

10. A health management cuff as set forth in claim 1 wherein said dividing segment is further defined by a strand segment interconnecting said opposing strand sections.

11. A health management cuff as set forth in claim 10 wherein said strand segment is magnetic.

12. A health management cuff as set forth in claim 10 wherein said strand segment is non-magnetic.

13. A health management cuff as set forth in claim 12 wherein said opposing strand sections are magnetic.

14. A health management cuff as set forth in claim 10 wherein said strand segment is further defined by a sleeve formed from a magnetic material to receive said strand extending therethrough with said sleeve mechanically connected to said strand.

15. A health management cuff as set forth in claim 1 wherein each bead includes an opening for receiving said strand.

16. A health management cuff as set forth in claim 15 wherein each bead signifies a fragmental value of said health management system.

17. A health management cuff as set forth in claim 16 wherein said fragmental value represents a numerical value.

18. A health management cuff as set forth in claim 16 wherein said fragmental value represents a non-numerical value.

19. A health management cuff as set forth in claim 1 including a male connector and a female connector selectively connected to each opposing strand section to mechanically engage said opposing strand sections.

20. A health management cuff as set forth in claim 1 wherein said dividing segment is further defined by a plurality of parallel tracks spaced one from another interconnecting said opposing strand section.

21. A health management cuff as set forth in claim 20 wherein said plurality of parallel tracks includes five tracks.

22. A health management cuff as set forth in claim 20 wherein each of said plurality of parallel tracks includes a device disposed along each track to divide each track into opposing halves.

23. A health management cuff as set forth in claim 22 wherein said device is further defined by a pair of curved resilient members each presenting terminal ends.

24. A health management cuff as set forth in claim 23 wherein said device further includes a pair of fasteners with each fastener clamping said spaced resilient members at the respective terminal ends thereby connecting said spaced resilient members to each of said opposing halves of each track.

25. A health management cuff as set forth in claim 24 wherein said opposing strand sections are formed from a non-metallic material.

26. A health management cuff as set forth in claim 25 wherein said non-metallic material includes leather.

27. A health management cuff as set forth in claim 25 wherein said non-metallic material includes polymer.

28. A health management cuff as set forth in claim 27 wherein said plurality of beads are selectively retained on said tracks.

* * * * *